United States Patent [19]

DeLuca et al.

[11] Patent Number: 5,585,369
[45] Date of Patent: Dec. 17, 1996

[54] METHOD OF TREATING LOW BONE TURNOVER OSTEOPOROSIS WITH (20S) VITAMIN D COMPOUNDS

[75] Inventors: Hector F. DeLuca, Deerfield, Wis.; Jerzy Wicha, Warsaw, Poland

[73] Assignee: Wisconsin Alumni Research Foundation, Madison, Wis.

[21] Appl. No.: 437,130

[22] Filed: May 5, 1995

Related U.S. Application Data

[62] Division of Ser. No. 148,203, Nov. 3, 1993.

[51] Int. Cl.$^6$ .................................................. A61K 31/59
[52] U.S. Cl. ............................................. 514/167
[58] Field of Search ............................... 514/167

[56] References Cited

U.S. PATENT DOCUMENTS

| | | | |
|---|---|---|---|
| 4,421,690 | 12/1983 | Partridge et al. | 552/653 |
| 4,590,184 | 5/1986 | Maeda et al. | 514/167 |
| 4,594,432 | 6/1986 | Baggiolini et al. | 552/653 |
| 4,613,594 | 9/1986 | Baggiolini et al. | 514/167 |
| 4,851,401 | 7/1989 | DeLuca et al. | 514/167 |
| 4,929,609 | 5/1990 | Batcho et al. | 514/167 |
| 5,247,104 | 9/1993 | DeLuca et al. | 552/653 |
| 5,393,749 | 2/1995 | DeLuca et al. | 514/167 |
| 5,401,731 | 3/1995 | Calverley et al. | 514/167 |
| 5,401,732 | 3/1995 | Calverley et al. | 514/167 |
| 5,446,034 | 8/1995 | Bretting et al. | 514/167 |
| 5,447,924 | 9/1995 | Bretting | 514/167 |
| 5,449,668 | 9/1995 | Sestelo | 514/167 |

FOREIGN PATENT DOCUMENTS

WO91/00271 6/1990 WIPO.

OTHER PUBLICATIONS

Calverley, et al "Vitamin D" in *Antitumor Steroids* by R. T. Blickenstaff (1992) pp. 193–270.

*Primary Examiner*—Kimberly J. Prior
*Attorney, Agent, or Firm*—Andrus, Sceales, Starke & Sawall

[57] ABSTRACT

The present invention is directed toward the use of 20-epi-vitamin $D_3$ analogs to treat low bone turnover osteoporosis. The 20-epi compounds are characterized by a marked intestinal calcium transport activity while exhibiting much higher activity than $1\alpha,25$-dihydroxyvitamin $D_3$ in their ability to mobilize calcium from bone.

5 Claims, No Drawings

METHOD OF TREATING LOW BONE TURNOVER OSTEOPOROSIS WITH (20S) VITAMIN D COMPOUNDS

This invention was made with United States Government support awarded by the National Institutes of Health (NIH), Grant No. DK-14881. The United States Government has certain rights in this invention.

This application is a divisional of copending application Ser. No. 08/148,203 filed Nov. 3, 1993.

This invention relates to biologically active vitamin D compounds. More specifically, the invention relates to (20S) vitamin D compounds, to a general process for their preparation, and to their use in treating osteoporosis.

With the discovery of 1α,25-dihydroxyvitamin $D_3$, as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin $D_3$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of 1α,25-dihydroxyvitamin $D_2$ in the epi-configuration appears to diminish activity in the mobilization of calcium from bone. On the other hand, increased hydrophobicity on the 26- and 27-carbons seems to increase the total activity of the vitamin D compounds provided the 25-hydroxyl is present.

Several of these known compounds exhibit highly potent activity in vivo or in vitro, and possess advantageous activity profiles. Thus, some of these compounds are in use, or have been proposed for use, in the treatment of a variety of diseases such as renal osteodystrophy, vitamin D-resistant rickets, osteoporosis, psoriasis, and certain malignancies.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally, the disease, which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (corticosteroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fact of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., 1α-hydroxyvitamin $D_3$, 1α,25-hydroxyvitamin $D_2$ 1α,25-dihydroxyvitamin $D_3$, 1α,25-dihydroxyvitamin $D_2$ and 1,24,25-trihydroxyvitamin $D_3$, although capable of the activity described and claimed in that patent are also characterized by the disadvantage of causing hypercalcemia especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and 1α-hydroxyvitamin $D_3$ for treatment of osteoporosis in a general expression of utility for those compounds. It is well known both of those compounds express traditional vitamin D-like activity, including the danger of hypercalcemia.

U.S. Pat. No. 4,588,716 also suggests the use of 1α,25-dihydroxy-24-epi-vitamin $D_2$ to treat bone disorders characterized by the loss of bone mass, such as osteoporosis. This compound expresses some of the vitamin D-like characteristics affecting calcium metabolism such as increasing intestinal calcium transport and stimulating the mineralization of new bone. It also has the advantage of minimal effectiveness in mobilizing calcium from bone. The 24-epi compound may be administered alone or in combination with a bone mobilization inducing compound such as a hormone or vitamin D compound such as 1α-hydroxyvitamin $D_3$ or $D_2$ or 1α,25-dihydroxyvitamin $D_3$ or $D_2$.

U.S. Pat. No. 5,194,431 discloses the use of 24-cyclopropane vitamin $D_2$ compounds in treating osteoporosis. Also, U.S. Pat. No. 4,851,401 discloses the use of cyclopentano 1,25-dihydroxyvitamin $D_3$ compounds in the treatment of osteoporosis and related diseases.

In an ongoing effort to develop a treatment for osteoporosis, the carbon 20 position of the side-chain was investigated to determine its potential. Altering the order of substituents or the substitution pattern on carbon 20 could result in a change of minimum energy position for conformations around the $C_{17}$–$C_{20}$ bond, and consequently, in a change of side-chain orientation with respect to the ring system. Orientation of the side-chain with respect to the ring system and configuration on the $C_{20}$ may have important consequences for biological properties of cholestane derivatives, in particular vitamin D compounds. It is well documented that binding of 1α,25-dihydroxyvitamin $D_3$ (1, Scheme 1) involves active centers in the ring A and triene system as well as in the side-chain. Altering the "normal configuration" around ($C_{17}$–$C_{20}$ bond in vitamin D could change the distance between active centers within the molecule, and thus result in a change in activity of such compounds.

SUMMARY OF THE INVENTION

The present invention provides (20S) vitamin D compounds exhibiting a desired, and highly advantageous, pattern of biological activity. These compounds are characterized by a marked intestinal calcium transport activity, almost equal to that of 1α,25-dihydroxyvitamin D₃, while exhibiting much higher activity than 1α,25-dihydroxyvitamin D₃ in their ability to mobilize calcium from bone. Hence, these compounds are highly specific in their calcemic activity. Their preferential activity on intestinal calcium transport and markedly high calcium mobilizing activity in bone allows the in vivo administration of these compounds for the treatment of metabolic bone diseases where bone turnover is a major concern. Because of their preferential calcemic activity, these compounds would be preferred therapeutic agents for the treatment of diseases, such as low bone turn over osteoporosis, and hypoparathyroidism.

Structurally, the key feature of the compounds having these desirable biological attributes is that they are analogs of 1,25-dihydroxyvitamin D₃ in which the methyl group normally attached to the side-chain at carbon 20 is in the epi configuration. This "unnatural" configuration about carbon 20 represents an exchange of the methyl and hydrogen radicals from the "natural" C-20 configuration. Thus, the compounds of this type are characterized by the following general structure:

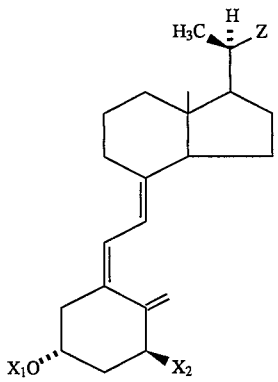

where the stereochemical center at carbon 20 in the side chain has the S configuration, $X_1$ may be hydrogen or a hydroxy-protecting group, $X_2$ may be hydrogen, hydroxy, or protected hydroxy, and where Z is selected from the group consisting of Y, —OY, —CH₂OY, —C≡CY and —CH=CHY, where the double bond may have the cis or trans stereochemical configuration, and where Y is selected from the group consisting of hydrogen, methyl, —CR₅O and a radical of the structure

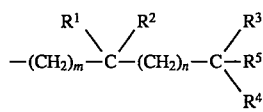

where m and n, independently, represent the integers from 0 to 5, where $R^1$ is selected from the group consisting of hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently, is selected from the group consisting of hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group, =CR₂R₃, or the group —(CH₂)$_p$—, where p is an integer from 2 to 5, and where $R^3$ and $R^4$, taken together, represent an oxo group, or the group —(CH₂)$_q$—, where q is an integer from 2 to 5, and where $R^5$ represents hydrogen, hydroxy, protected-hydroxy, or $C_{1-5}$ alkyl.

The present invention, therefore, provides compounds showing preferential activity on intestinal calcium transport and increased calcium mobilizing activity in bone, and are useful for the treatment of hypoparathyroidism as well as metabolic bone disease, such as low bone turn over osteoporosis, where bone turnover is a major concern. More specifically, the preferred compound is (20S) 1α,25-dihydroxyvitamin D₃.

This invention also provides novel intermediate compounds formed during the synthesis of the end products. Some of the intermediate compounds are characterized by the following general structure:

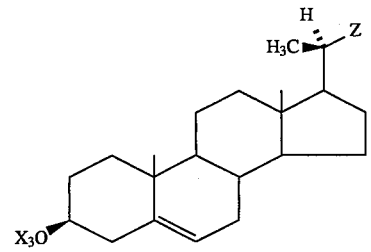

where the stereochemical center at carbon 20 in the side chain has the S configuration, $X_3$ may be hydrogen or a hydroxy-protecting group, and Z is as previously defined herein.

Other key intermediates are characterized by the following general structure:

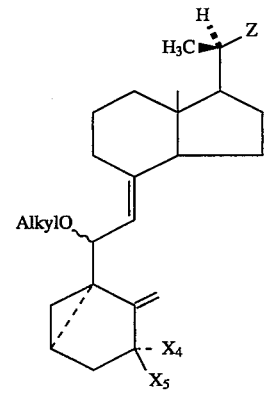

where the stereochemical center at carbon 20 in the side chain has the S configuration, $X_4$ and $X_5$, which may be the same or different, is hydrogen, hydroxy, or oxygen, and Z is as previously defined herein.

In another aspect of the invention, it has now been found that the loss of bone mass, which is characteristic of osteoporosis may be effectively treated by the administration of a (20S) vitamin D compound in sufficient amounts to increase bone mass. More specifically, a method of treating low bone turn over osteoporosis comprises the administration of an effective amount of a (20S) vitamin D compound, preferably (20S) 1α,25-dihydroxyvitamin D₃. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will restore bone mass due to the preferential calcemic activity of these compounds. Further, these compounds advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of (20S) vitamin D compounds such as (20S) 1α,25-dihydroxyvitamin $D_3$ is effective in restoring or maintaining bone mass, and thus provides a novel method for the treatment or prevention of various forms of osteoporosis, in particular low bone turn over osteoporosis. It will be evident that the method will find ready application for the prevention or treatment of disease states other than those named, such as hypoparathyroidism.

DETAILED DESCRIPTION OF THE INVENTION

As used in the description and in the claims, the term hydroxy-protecting group signifies any group commonly used for the temporary protection of hydroxy functions, such as for example, alkoxycarbonyl, acyl, alkylsilyl, and alkoxyalkyl groups, and a protected hydroxy group is a hydroxy function derivatized by such a protecting group. Alkoxycarbonyl protecting groups are groupings such as methoxycarbonyl, ethoxycarbonyl, propoxycarbonyl, isopropoxycarbonyl, butoxycarbonyl, ixobutoxycarbonyl, tert-butoxycarbonyl, benzyloxycarbonyl or allyloxycarbonyl. The term 'acyl' signifies an alkanoyl group of 1 to 6 carbons, in all of its isomeric forms, or a carboxyalkanoyl group of 1 to 6 carbons, such as an oxalyl, amlonyl, succinyl, glutaryl group, or a aromatic acyl group such as benzoyl, or a halo, nitro or alkyl substituted benzoyl group. The word 'alkyl' as used in the description or the claims, denotes a straight-chain or branched hydrocarbon radical of 1 to 10 carbons, in all its isomeric forms. Alkoxyalkyl protecting groups are groupings such as methoxymethyl, ethoxyethyl, methoxyethoxymethyl, or tetrahydrofuranyl and tetrahydropyranyl. Preferred alkylsilyl protecting groups are trimethylsilyl, triethylsilyl, t-butyldimethylsilyl, and analogous alkylated silyl radicals.

The vitamin D compounds useful in the present treatment are (20S) vitamin D compounds, preferably (20S) 1α,25-dihydroxyvitamin $D_3$. The above compounds may be administered alone or in combination with other pharmaceutically acceptable agents.

The vitamin D compounds or combinations thereof can be readily administered as sterile parenteral solutions by injection or intravenously, or by alimentary canal in the form of oral dosages, or transdermally, or by suppository. Doses of from about 0.5 micrograms to about 50 micrograms per day of the compounds per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient amounts of the compound should be used to restore bone mass. Amounts in excess of about 50 micrograms per day or the combination of that compound with other 1α-hydroxylated vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art. For example, to be effective, the (20S) 1α,25-dihydroxyvitamin $D_3$ compound is preferably administered in a dosage range of 0.5–50 μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The present invention is more specifically described by the following examples, which are meant to be illustrative only of the process of synthesis and of the compounds, both end products and intermediates, obtainable thereby. In these examples, specific compounds identified by Arabic numerals (e.g. compounds 1, 2, 3 . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease.

Chemistry

The synthetic route to (20S) 1α,25-dihydroxyvitamin $D_3$ 2a, which includes (20S) 25-hydroxycholesterol acetate 7a, (20S) vitamin $D_3$ derivative 10a and 3,5-cyclo-9,10-seco-derivatives 11a and 11b as key intermediates was chosen.

(20S) 25-hydroxycholesterol acetate 8 was synthesized by the method involving alkylation of pregnenoic esters, allowing for stereoselective synthesis of the (20R), Wicha et al, J. Chem. Soc., Perkin 1, 1978, 1282, or the (20S), Wicha et al, Synth. Commun., 1989, 19, 63, series.

Ester 4 readily available from commercial androstane derivative 3, Wicha et al, Synth. Commun., 1977, 7, 215–222, was treated with lithium diisopropylamide and then with methyl iodide to give the methyl derivative 5 in virtually quantitative yield and with at least 95% diastereoisomeric selectivity. Ester 5 was reduced with lithium aluminiumhydride; the corresponding alcohol 6a was converted to the tosyl derivative 6b which was subjected to reaction with the lithium derivative of 3-methyl-1-butyn-3-yl 2-tetrahydropyranyl ether, Barton et al, J. Chem. Soc., (C), 1970, 1584 and Uskokovic et al, Helv. Chim. Acta, 1974, 57, 768, to give compound 7a with 8-carbon sidechain. Acetylenic bond in 7a was saturated under usual conditions and the product 7b was solvolized in glacial acetic acid to give the intermediate 8.

Bromination-dehydrobromination of compound 8 followed by treatment of the crude product with PTSA in dioxane and chromatography on a silica gel column, Uskokovie et at, J. Org. Chem., 1981, 46, 1030, afforded pure acetoxy diene 9a in a 47% yield. The respective alcohol 9b was subjected to photolysis using a medium-pressure UV lamp equipped with a Vycor filter. The reaction was monitored with HPLC and was stopped at the ca. 50% of conversion of the starting diene. The crude product was heated in ethanol at 75° C. for 6 h and then chromatographed on a silica gel column. A mixture of diene 9b and triene 10a was obtained which could not be separated into components. This mixture was treated with tosyl chloride to give a mixture of the corresponding 3-tosylates which were reacted with methanol in the presence of sodium hydrogen carbonate, Sheyes et al. J. Am. Chem. Soc., 1975, 97, 6249. Careful chromatography of the reaction product afforded the 3,5-cyclo-6-methoxy derivative 11a.

The intermediate 11a was transformed into the target compound 2a using the methodology of Paaren et al, J. Org. Chem., 1980, 45, 3253; DeLuca et al U.S. Pat. No. 4,555,364; and Kutner et al, J. Org. Chem., 1988, 53, 3454. Hydroxylation of compound 11a with seleninum dioxide gave a mixture of 1β-hydroxy derivative 11b and α,β-unsaturated ketone 11c, which was separated by chromatography. Solvolysis in acetetic acid of compound 11b allowed to recover the triene system and, finally, the ester group in 2b was hydrolyzed to the (20S) vitamin $D_3$ analogue 2a which was purified by HPLC.

Experimental

Melting points were determined on a Thomas Hoover capillary melting point apparatus and are uncorrected. Spectra were recorded using the following instruments: $^1$H NMR-Brucker AM 400 or AM 500, as indicated (for deuteriumchloroform solutions with tetramethylsilane as an integral standard), UV- Perkin-Elmer Lambda 3B uv/vis (for ethanol solutions), mass and high resolution mass—Kartos MS-50Ts (70 eV). Ail reactions involving dienes or trienes were carried out under argon. Organic solutions were dried over anhydrous sodium sulfate and solvents were evaporated on a rotary evaporator. Column chromatography was performed using silica gel, Merck, 60, 230–400 mesh and preparative layer chromatography (PLC) using precoated silica gel plates, 20×20×0.025 cm, Merck. For high pressure liquid chromatography (HPLC) Waters Associated 6VK instrument equipped with Zorbax silica column (6.2 mm×20 cm) was used.

Ethyl 6β-methoxy-3α,5-cyclo-5α-pregnan-21-oate
(4)

A mixture of ethyl 6β-methoxy-3α, 5-cyclo-5α-pregn-17 (20)-en-21-oate (7.15 g), Wicha et al, J. Org. Che., 1990, 55, 3484, platinum oxide (0.30 g) and ethanol (60 ml) was stirred under hydrogen for 16 h. Usual workup gave saturated ester 4 (7.20 g, 100%), an oil;
$^1$H NMR(500)δ(ppm) 4.11(2H, q, J=7.1 Hz, $OCH_2CH_3$), 3.33(3H, s, $OCH_3$), 2.77(1H, t, J=2 Hz, $C_6$-H), 1.25(3H, t, J=7.1 Hz, $OCH_2CH_3$), 1.03(3H, s, $C_{19}$-H), 0.65(3H, s, $C_{18}$-H) overlapping 0.63–0.57(1H, m, cyclopropane H), 0.43(1H, dd, $J_1$=8.0, $J_2$=5.3 Hz, cyclopropane H).
High resolution mass spec. for $C_{24}H_{38}O_3$ calcd.: 374.2821($M^+$);
found 374.2818, 359.2583($M^+$—$CH_3$, 43%), 342.2546($M^+$—$CH_3OH$, 100%), 329.2470($M^+$—$C_2H_5O$, 16%), 319.2280($M^+$—$C_4H_9$, 77%).

(20R) Ethyl
6β-methoxy-24,25-bisnor-3α,5-cyclo-5α-cholan-22-oate
(5)

To a mixture of diisopropyl amine (0.91 ml, 6.5 mmol) and THF (10 ml), stirred under argon, n-butyllithium (1.6 M in hexane, 4.0 ml, 6.5 mmol) was added at −20° C. After 30 min the reaction mixture was cooled to −78° C. and a solution of ester 4 (1.60 g, 4.3 mmol) in THF (7 ml) was added during 20 min. After a further 40 min., methyl iodide (0.81 ml, 13.0 mmol) in hexamethylphosphoramide (4 ml) was added during 20 min. After 6 h the cooling bath was removed and the reaction mixture was set aside for 16 h. Usual workup and drying of the crude product in high vacuum afforded compound 5 (1.69 g, 100% yield) which was used for the next step without purification;
$^1$H NMR(500)δ 4.15–4.05(2H, m, $OCH_2CH_3$), 3.32(3H, s, $OCH_3$), 2.77(1H, br s, $C_6$-H), 2.32(1H, dr, $J_1$=10.9, $J_2$=7 Hz, $C_{20}$-H), 1.28(3H, t, J=7.2 Hz, $OCH_2CH_3$), 1.10(3H, d, J=6.8 Hz, $C_{21}$-H), 1.01(3H, s, $C_{19}$-H) 0.74(3H, s, $C_{18}$-H), 0.64(1H, t, J=4.3 Hz, cyclopropane H), 0.43(1H, dd, $J_1$=7.8, $J_2$=5.2 Hz, cyclopropane H); signal which presumably corresponds to $C_{21}$-H of the (20S) isomer appeared at 1.00 ppm, integrating for less than 5%; High resolution mass spec. for $C_{25}H_{40}O_3$ calcd.: 388.2977($M^+$);
found: 388.2972(64%), 373.2733($M^+$—$CH_3$, 53%), 356.2751 ($M^+$—$CH_3OH$, 100%), 333.2430($M^+$—$C_4H_9$, 88%).

(20R)

22-Hydroxy-6β-methoxy-23,24-bisnor-3α,5-cyclo-5α-cholane (6a)

A mixture of ester 5 (1.34 g), lithiumaluminium hydride (0.5 g) and ether (20 ml) was heated under reflux for 1 h. The reagent excess was decomposed with saturated aqueous $Na_2SO_4$ and the product was isolated in the usual way. Alcohol 6a was obtained (1.17 g, 98% yield); a sample was purified by PLC (hexane—ethyl acetate, 8:3);
$^1$H NMR (500) δ 3.73(1H, dd, $J_{22a,22b}$=10.6, $J_{22a,20}$=3.4 Hz, $C_{22}$-Ha), 3.48(1H, dd, $J_{22b,22a}$=10.7, $J_{22b,20}$=7 Hz, $C_{22}$-Hb), 3.32(3H, s, $OCH_3$), 2.77(1H, t, J=2.6 Hz, $C_6$-H), 1.02(3H, s, $C_{19}$-H), 0.96(3H, d, J=6.7 Hz, $C_{21}$-H), 0.74(3H, s, $C_{18}$-H), 0.65(1H, dd, $J_1$=$J_2$=4.3 Hz) and 0.43(1H, dd, $J_1$=7.9, $J_2$=5.1 Hz, cyclopropane H).
High resolution mass spec. for $C_{23}H_{38}O_2$ calcd.: 346.2860($M^+$); found: 346.2860; 331.2623($M^+$—$CH_3$, 72%), 314.2613($M^+$—$CHaOH$, 89%); 291.23 19($M^+$—$C_4H_9$, 100%).

(20R)

22-Tosyloxy-6β-methoxy-23,24-bisnor-3α,5-cyclo-5α-cholane (6b)

The reaction was performed according to the general procedure developed by Partridge et al, Helv. Chim. Acta, 1974, 57, 768, using the reagents as follows: alcohol 6a (1.21 g) in pyridine (1.4 ml) and tosyl chloride (0.9 g) in pyridine (1.4 ml). Tosylate 6b (1.61 g, 92% yield) was obtained;
$^1$H NMR (500) δ 7.79(2H, d, J=8.2 Hz) and 7.34(2H, d, J=8.1 Hz, aromatic H) 4.12(1H, dd, $J_1$=9.3, $J_2$=3.5 Hz, $C_{22}$-Ha), 3.82(1H, dd, $J_1$=9.2, $J_2$=7.3 Hz, $C_{22}$-Hb), 3.31(3H, s, $OCH_3$), 2.76(1H, br s, $C_6$-H), 2.45(3H, s, $C_6H_4CH_3$), 1.00(3H, s, $C_{19}$-H), 0.88(3H, d, J=6.6 Hz, $C_{21}$-H), 0.63(3H, s, $C_{18}$-H) overlapping (1H, m, cyclopropane H), 0.44(1H, dd, $J_1$=7.9, $J_2$=5.2 Hz, cyclopropane H).
High resolution mass spec. for $C_{30}H_{44}O_4S$ calcd.: 500,2969 ($M^+$);
found: 500,2960(41%), 485.2740($M^+$—$CH_3$, 32%), 445.2400($M^+$—$C_4H_9$, 57%).

(20S)

6β-Methoxy-25-(tetrahydropyranyl-2-oxy)-3α,5-cyclo-5E-cholest-23-yne (7a)

To a stirred under argon solution of 3-methyl-1-butyn-3-yl 2-tetrahydropyranyl ether (1.68 g. 6.1 mmol) Barton et al, j. Chem. Soc., (C), 1970, 1584, (1.68 g, 6.1 mmol) in anhydrous dioxane (45 ml), n-butyllithium (1.6M in hexane, 3.8 ml, 6.1 mmol) was added at 5° C. The mixture was stirred at 5° C. for 1.5 h and then at room temperature for 1.5 h whereupon tosylate 6b (0.61 g, 1.22 mmol) in dioxane (10 ml) was added. The mixture was heated under reflux for 72 h, cooled and poured into water containing an excess of ammonium chloride. The product was extracted with ethyl acetate. The extract was washed with water and with brine. The solvent was evaporated and the residue (0.95 g) was dried in high vacuum for 16 h to give the crude product 7a (0.77 g). A sample was purified by PLC (hexane—ethyl acetate, 20:1);
$^1$H NMR (500) δ 5.07(1H, br s, THP acetal H), 4.00–3.58(1H, m) and 3.50–3.40(1H, m, THP-H), 3.32(3H, s, OCH$_3$), 2.77(1H, br s, C$_6$-H), 1.57 and 1.46(6H, 2s, C$_{26}$- and C$_{27}$-H), 1.02(3H, s, C$_{19}$-H, 0.9720 and 0.9689(3H, 2d, J=6.7 Hz, C$_{21}$-H), 0.72(3H, s, C$_{19}$-H), 0.53–0.51(1H, m, cyclopropane H), 0.50–0.45(1H, m, cyclopropane H).
High resolution mass spec. for C$_{33}$H$_{52}$O$_3$ calcd.: 496.3916(M$^+$); found: 496.3620(2.5%).

(20S)

6β-Methoxy-25-(tetrahydropyranyl-2-oxy)-3α,5-cyclo-5α-cholestane (7b)

A mixture of the crude acetylene derivative 7a (0.38 g), 5% palladium on activated carbon (0.05 mg), NaHCO$_3$ (0.60 mg) and dioxane (20 ml) was stirred under hydrogen for 24 h. The solid was filtered off and the solvent was removed to give saturated product 7b (0.38 g). A sample was prepared by preparative TLC (hexane—ethyl acetate, 4:1).
$^1$H NMR (500) δ 4.74–4.70(1H, br S, THP acetal H), 4.00–3.95(1H, m) and 3.50–3.45(1H, m, THP-H), 3.33(3H, s, OCH$_3$), 2.77(1H, br s, C$_6$-H), 1.26 and 1.21(6H, 2s, C$_{26}$- and C$_{27}$-H) 1.03(3H, s, C$_{19}$-H), 0.83(3H, d, J=6.5 Hz, C$_{21}$-H), 0.72(3H, s, C$_{18}$-H), 0.66–0.64(1H, m, cyclopropane H), 0.43(1H, dd, J$_1$=8, J$_2$=5.1 Hz, cyclopropane H).
High resolution mass spec. for C$_{33}$H$_{56}$O$_3$ calcd.: 500.4229 (M$^+$);
found: 500.4234 (4%).

(20S)

3β,25-Hydroxycholest-5-ene 3-acetate (8)

A solution of the crude methoxy derivative 7b (0.38 g) in acetic acid (30 ml) was stirred at 70° C. for 2 h, cooled and set aside for 16 h. Acetic acid was evaporated on a rotary evaporator, the residue was taken in ethyl acetate (60 ml), washed with aqueous NaHCO$_3$ and with brine. Solvent was evaporated and the residue (0.34 g) was chromatographed on silica gel (40 g, hexane—ethyl acetate, 5:1) to give acetate 8 (0.16 g, 69% yield from tosylate 6b);
$^1$H NMR (400) δ 5.40–5.35(1H, m, C$_6$-H), 4.65–4.55(1H, m, C$_3$-H), 2.03(3H, s, COCH$_3$), 1.21(6H, s, C$_{26}$- and C$_{27}$-H), 1.10(3H, S, C$_{19}$-H), 0.84(3H, d, J=6.6 Hz, C$_{21}$-H), 0.77(3H, s, C$_{18}$-H).

Mass spec. m/z 384(M$^+$—CH$_3$CO$_2$H; high resolution mass spec. for C$_{27}$H$_{44}$O(M$^+$—CH$_3$CO$_2$H) calcd.: 384.3392; found: 384.3389(100%), 366.3273(M$^+$—CHaCO$_2$H—H$_2$O, 17%)

(20S)

3β,25-Dihydroxycholesta-5,7-diene 3-acetate (9a)

A mixture of ene 8 (0.16 g), powderized NaHCO$_3$ (0.18 g), 1,3-dibromo-5,5-dimethylhydantoin (0.08 g) and hexane (5 ml) was stirred at the reflux temperature for 25 min. After cooling, the solid was filtered off under argon and washed with hot hexane. Combined filtrates were evaporated. To the residue xylene (10 ml) and collidine (1 ml) were added, the mixture was heated under reflux for 1.5 h, cooled and poured into water. The product was extracted with ether (3×20 ml). Combined extracts were washed consecutively with cold 5% HCl (twice), water, aqueous NaHCO$_3$ and brine. Bulk of the solvent was evaporated. The residue containing the initially used xylene was diluted with toluene (50 ml) and ethanol (50 ml) and evaporated. Remaining thick oil was dried in high vacuum and then it was dissolved in dioxane (10 ml) containing p-toluenesulphonic acid (10 mg). The solution was kept at 55° C. for 4 h whereupon it was diluted with ethyl acetate (30 ml). The product was isolated in the usual way and chromatographed on silica gel (24 g, hexane—ethyl acetate, 4:1). Fractions containing 5,7-diene were collected to give the title compound 9a (0.075 g, 47% yield); λ$_{max}$ 240, 249, 260 and 272 nm;
$^1$H NMR (500) δ0 5.57(1H, dd, J$_{6,7}$=6, J$_{6,4a}$=2 Hz, C$_6$-H), 5.39(1H, dt, J$_{7,6}$=6, J$_{7,9}$=J$_{7,14}$=2 Hz, C$_6$-H), 4.70(1H, tt, J$_1$=11, J$_2$4.5 Hz, C$_3$-H), 2.01(3H, s, COCH$_3$), 1.22(6H, s, C$_{26}$- and C$_{27}$-H), 0.95(3H, s, C$_{19}$-H), 0.85(3H, d, J=6.5 Hz. C$_{21}$-H), 0.52(3H, s, C$_{18}$-H).
Mass spec. m/z 442(M$^+$, 5%), 424(M$^+$—H$_2$O, 7%), 382(M$^+$ —CH$_3$CO$_2$H, 100%), 364(M$^+$—CH$_3$CO$_2$H—H$_2$O, 3%).

(20S)

25-Hydroxy-6ξ-methoxy-3α,5β-cyclo-9,10-secocholesta-7E, 10(19)-diene (11a)

A solution of acetate 9a (75 mg) in ethanol (10 ml) containing 5% aqueous NaOH (1 ml) was set aside for 24 h and then the solvent was evaporated in vacuo. The residue was taken in ethyl acetate (30 ml) and washed consecutively with 5% HCl, water, and saturated aqueous NaHCO$_3$. Evaporation of the solvent gave (20S) 3b,25-dihydroxycholesta-5,7-diene 9b (74 mg) which was used for the next step without purification; λmax 240, 249, 260 and 272 nm; high resolution mass spec. for C$_{27}$H$_{44}$O$_2$ calcd.: 400.3341(M$^+$); found: 400.3334(100%), 398.3162(M$^+$— H$_2$O, 1.1%), 385.3101(M$^+$—CH$_3$, 14%), 380.3086, 24%), 367.3013(M$^+$—CH$_3$—H$_2$O, 67%).

A solution of this product 9b in benzene—ether (2:8, 120 ml), cooled in ice-water bath, was irradiated with a Hanovia 608A36 medium-pressure UV lamp equipped with a Vycor filter. After 15 min the solvent was evaporated and the residue was dissolved in ethanol (20 ml) and heated at 75° C. for 6 h. The solvent was removed and the residue was chromatographed on silica gel (8 g, hexane—ethyl acetate, 4:1) to give a mixture of seco-triene 10a and unchanged diene 9b (60 mg); TLC, hexane-ethyl acetate, 1:1, R$_f$=0.36.

To a solution of the above described alcohols (9b and 10a, 60 mg) in pyridine (0.5 ml), tosyl chloride (60 mg) was added at 0° C. and the reaction mixture was stirred at 0°–5°

C. for 16 h and then at room temperature for 2 h. Usual workup gave a mixture of the corresponding tosylates (65 mg) which was dried in high vacuum and then dissolved in anhydrous methanol (30 ml) containing sodium hydrogen carbonate (0.5 g). The mixture was set aside at 37° C. for 16 h whereupon it was stirred at 55 ° C. for 2 h. The product was recovered in the usual way and chromatographed on $SiO_2$ (5 g, hexane—ethyl acetate, 5:1). Appropriate fractions were collected to give "cyclovitamin" 11a (4.6 mg, 6.3% yield from acetoxy diene 9a);

$^1$H NMR (500) δ 5.04(1H, br s, $C_{19}$-Ha), 4.99(1H, d, $J_{7,6}$=9.2 Hz, $C_7$-H), 4.88(1H, br s, $C_{19}$-Hb), 4.16(1H, d, $J_{6,7}$=9.4 Hz, $C_6$—H), 3.26(3H, s, $OCH_3$), 1.22(6H, s, $C_{26}$— and $C_{27}$—H), 0.92(1H, dd, $J_1$=8.5, $J_2$=4.6 Hz, cyclopropane H), 0.85(3H, d, J=6.5 Hz, $C_{21}$—H), 0.74(1H, t, J=4.5, Hz, cyclopropane H), 0.53(3H, s, $C_{18}$—H).

High resolution mass spec. for $C_{28}H_{46}O_2$ calcd.: 414.3497($M^+$):
found: 414.3510(15%). 382.3242($M^+$—$CH_3OH$, 31%). 364.3113($M^+$—$CH_3OH$—$H_2O$, 13%).

(20 S)

1α,25-Dihydroxy-6ξ-methoxy-3α,5β-cyclo-9,10-secocholesta-7E, 10(19)-diene (11b)

and (20S)

25-hydroxy-6ξ-methoxy-1-oxo-3α,5β-cyclo-9,10-secocholesta-7E ,10(19)-diene (11c)

The described procedure, Paaren et al, J. Org. Chem., 1980, 45, 3253; DeLuca et al U.S. Pat. No. 4,555,364; and Kutner et al, J. Org. Chem., 1988, 55, 3454, for hydroxylation of cyclovitamin was used.

A mixture of selenium dioxide (Aldrich, 99.999%) (6 mg,), t-butylhydroperoxide (Aldrich, 3M in 2,2,4-trimethylpentane, 93 μL) and methylene chloride (1.7 ml) were stirred at room temperature for 30 min and then pyridine (10 μL) was added. After a few minutes methyledene derivative 11a (4.6 mg) in methylene chloride (1 ml) was added. The mixture was stirred for 1.5 h whereupon 10% aqueous NaOH was added, stirring was continued for 10 min and the mixture was diluted with methylene chloride (10 ml). Phases were separated and the organic phase was washed with 10% NaOH and brine. Evaporation of the solvent gave a residue (7 mg) which was chromatographed on silica gel (1.5 g, hexane—ethyl acetate, 5:1, 20 ml and then hexane—ethyl acetate, 4:1) to give (in order of elution):

1.1-oxo-derivative 11c (1 mg), $λ_{max}$=242 nm.
$^1$H NMR (400) δ 6.04(1H, br s, $C_{19}$—Ha), 5.62(1H, s, $C_{19}$—Hb) 5.03(1H, br d, $J_{7,6}$=9 Hz, $C_7$—H), 4.07(1H, d, $J_{6,7}$=9.3 Hz, $C_6$-H), 3.30(3H, s, $OCH_3$), 1.22(6H, s, $C_{26}$— and $C_{27}$—H), 0.85(3H, d, J=6.5 Hz, $C_{21}$-H) overlapping 0.95–0.80(1H, m, cyclopropane H), 0.59(1H, t, J=4.5 Hz, cyclopropane H), 0.48(3H, s, $C_{18}$-H);

High resolution mass spec. for $C_{28}H_{44}O_3$ calcd.: 428.3290($M^+$);
found: 428.3308(24%), 410.3213($M^+$—$H_2O$, 35%), 98.3 135($M^+$—$CH_2O$, 14%), 396.3028($M^+$—$CH_3OH$, 50%).

2. 1β-Hydroxy-derivative 11b (2 mg) which was used immediately for the next step; mass spec.: m/z 430($M^+$, 10%) 412($M^+$—$H_2O$, 10%), 398($M^+$—$CH_3OH$, 20%), 380($M^+$—$CH_3OH$—$H_2O$, 45%).

(20S)

1α,25-Dihydroxyvitamin $D_3$ 1-acetate (2b)

A solution of the 3,5-cyclo derivative 11b (2 mg) in acetic acid (15 ml) was stirred at 55° C. for 20 min whereupon acetic acid was evaporated in vacuo. The reside was dried in high vacuum to give a mixture of trienes 2b and its 5E isomer (2 mg) in a ratio ca. 2:1 by HPLC (4.5% iso-propanol in hexane), retention times 10.4 and 13.6 min, respectively contaminated with ca. 10% of compounds with retention times 10 and 12 min, presumably the corresponding 1β-hydroxy-derivatives.

The above described mixture (2b and the isomer) was dissolved in ethyl acetate (0.1 ml) and treated with a solution of maleic anhydride (2 mg) in ethyl acetate (0.2 ml). After 45 min (HPLC indicated practically complete consumption of the E-isomer), the mixture was diluted with ethyl acetate (15 ml) and washed with saturated $NaHCO_3$ and brine. The solvent was evaporated to give isomerically pure 2b (6 mg); a sample was purified by HPLC; $λ_{max}$ 264 nm; high resolution mass spec. for $C_{29}H_{46}O_4$ calcd.: 458.3396($M^+$); found: 458.3399(6%), 398.3185($M^+$—$CH_3CO_2H$, 36%), 380.3093($M^+$—$CH_3CO_2H$—$H_2O$, 29%), 365.2844($M^+$—$CH_3CO_2H$—$H_2O$—$CH_3$, 12%).

(20S)

1α,25-Dihydroxyvitamin $D_3$ (2a)

A solution of acetate 2b (6 mg) in ether (2 ml) and methanol (1 ml) was treated with $K_2CO_3$ (50 mg) at room temperature for 4 h. The mixture was diluted with ethyl acetate (15 ml) washed with water and evaporated to give residue (1 mg) which was purified by HPLC (hexane-isopropanol, 95:5) to give the title compound 2a (500 μg, amorphous solid); $λ_{max}$ 264 nm;
$^1$H NMR (400) δ 6.38(1H, br d, J=10.9 Hz, $C_6$—H), 6.02(1H, d, $J_{7,6}$=11.4 Hz, $C_7$—H), 5.33(1H, br s, $C_{19}$—$H_E$), 5.00(1H, br s, $C_{19}$—Hz), 4.47–4.40(1H, m, $C_1$—H), 4.25–4.20(1H, m, $C_3$—H), 1.20 (6H, s, $C_{26}$— and $C_{27}$—H), 0.85(3H, d, J=6.5 Hz, $C_{27}$—H), 0.57(3H, s, $C_{18}$—H); high resolution mass spec. for $C_{27}H_{44}O_3$ calcd.: 416.3290($M^+$); found: 416.3306(7%), 398.3210($M^+$—$H_2O$, 21%), 383.2972($M^+$—$H_2O$—$CH_3$, 4%), 380.3071($M^+$—$2H_2O$, 13%).

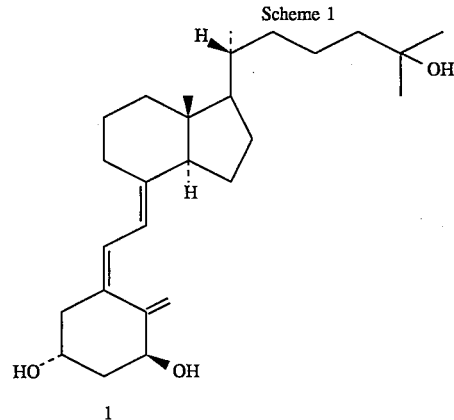

Scheme 1

1

13
-continued
Scheme 1
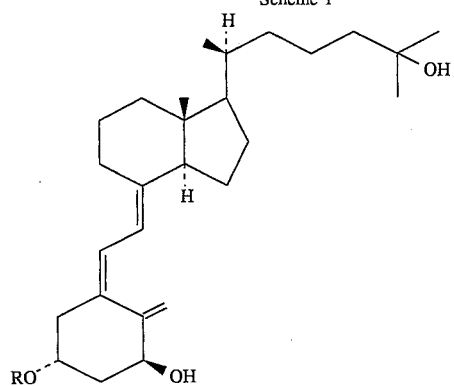
2a, R = H
2b, R = Ac
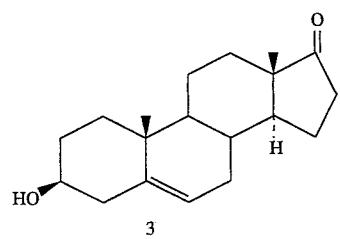
3
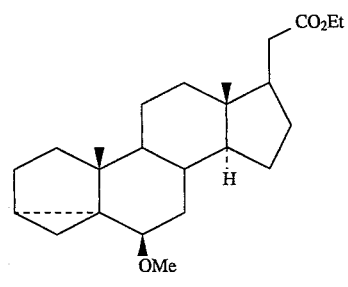
4
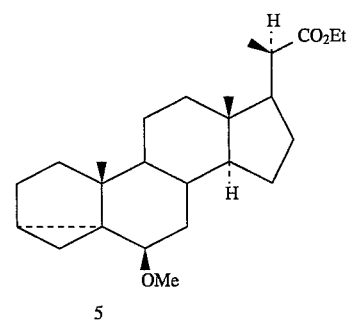
5
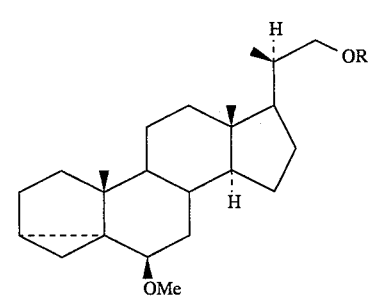
6a, R = H
6b, R = Ts
14
-continued
Scheme 1
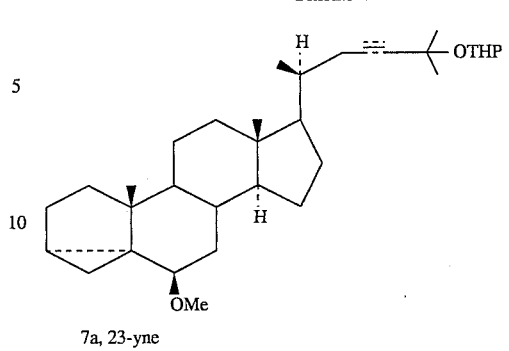
7a, 23-yne
7b, saturated
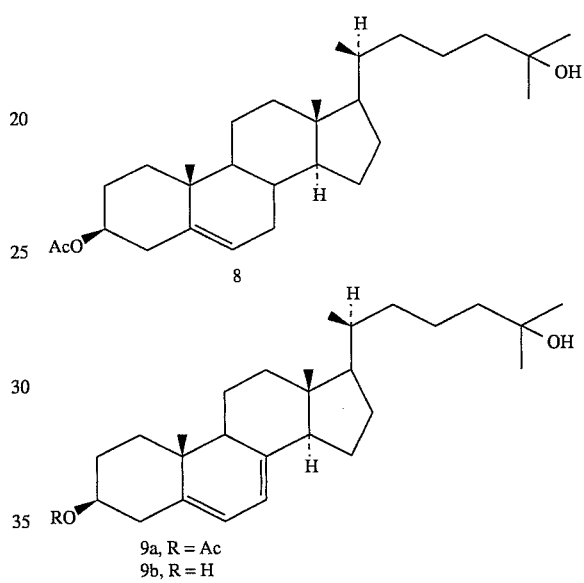
8
9a, R = Ac
9b, R = H
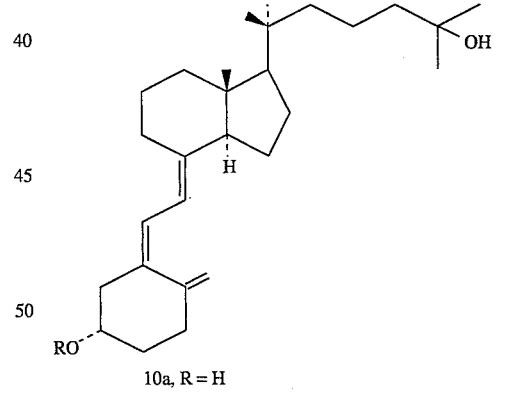
10a, R = H -continued
Scheme 1

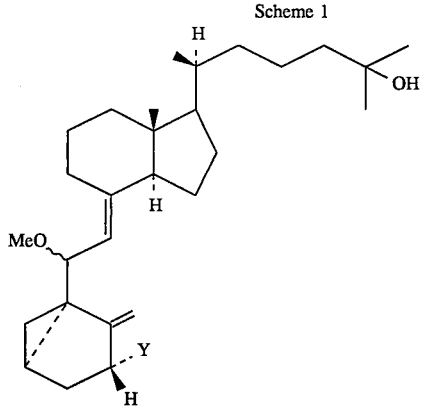

11a, X = Y = H
11b, X = OH, Y = H
11c, X, Y = O

Biological Activity

Rats were maintained on a normal calcium and normal phosphorus diet for one week (0.47% Ca, 0.3% P), then switched to a —Ca diet for the duration of the experiment (0.02% Ca). Vitamin D compounds were suspended in mixtures of ethanol and propylene glycol (5%:95%) and were administered daily for 7 days intraperitoneally.

After 7 days the rats were killed and the duodena were used for determination of intestinal calcium transport by the everted intestinal sac technique (Martin & DeLuca, 1967) and serum calcium (bone calcium mobilization). The tests were made against the 1,25-dihydroxyvitamin $D_3$ standard and are reported in Table 1.

TABLE 1

INTESTINAL CALCIUM TRANSPORT AND BONE CALCIUM MOBILIZING ACTIVITIES OF (20S) 1α,25-DIHYCROXYVITAMIN $D_3$

| Compound | Amount (μ/day/7 days) | S/M (Mean +/− SEM) | Serum Ca (Mean +/− SEM) (mg %) |
|---|---|---|---|
| —D | 0 | 4.7 +/− 0.31 | 4.2 +/− 0.09 |
| 1,25-(OH)$_2$D$_3$ | .025 | 8.6 +/− 0.56 | 4.7 +/− 0.10 |
|  | .075 | 10.1 +/− 0.36 | 5.9 +/− 0.13 |
| (20S) | .013 | 7.0 +/− 0.44 | 4.7 +/− 0.22 |
| 1,25-(OH)$_2$D$_3$ | .025 | 7.6 +/− 0.58 | 6.3 +/− 0.09 |
|  | .075 | 8.5 +/− 0.71 | 7.9 +/− 0.35 |

The results show that the (20S) 1,25-dihydroxyvitamin $D_3$ compound is slightly less active than 1,25-dihydroxyvitamin $D_3$ in intestinal calcium transport. However, the (20S) 1,25-dihydroxyvitamin $D_3$ compound has highly significant calcium mobilizing activity. The amount of bone calcium mobilizing activity is considerably greater than 1,25-dihydroxyvitamin $D_3$. These compounds therefore, by showing activity on intestinal calcium transport and increased calcium mobilizing activity in bone suggest that they are preferred agents for the treatment of a disease such as low bone turn over osteoporosis, as well as hypoparathyroidism.

For treatment purposes, the compounds of this invention may be formulated for pharmaceutical applications as a solution in innocuous solvents, or as an emulsion, suspension or dispersion in suitable solvents or carriers, or as pills, tablets or capsules together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 μg to 50 μg per day of the compounds are appropriate for treatment purposes, such doses being adjusted according to the disease to be treated, its severity and the response of the subject, as is well understood in the art. Since the (20S) compounds exhibit specificity of action, each may be suitably administered alone, in situations where only bone mobilization stimulation is desired, or together with graded doses of another active vitamin D compound—e.g. 1α-hydroxyvitamin $D_2$ or $D_3$, or 1α,25-dihydroxyvitamin $D_3$—in situations where some degree of additional calcium transport stimulation is found to be advantageous.

Various modes of carrying out the invention are contemplated as being within the scope of the following claims particularly pointing out and distinctly claiming the subject matter regarded as the invention.

We claim:

1. A method of treating metabolic bone disease where it is desired to maintain or increase bone mass by increasing bone turnover comprising administering to a patient with said disease a compound having the formula

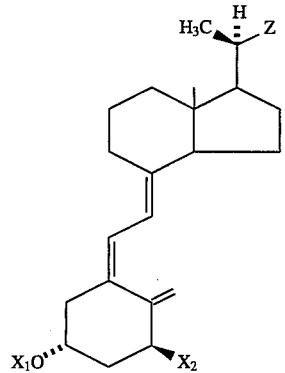

where the stereochemical center at carbon 20 in the side chain has the S configuration, $X_1$ may be hydrogen or a hydroxy-protecting group, $X_2$ may be hydrogen, hydroxy, or protected-hydroxy, and where Z is selected from the group consisting of Y, —OY, —CH$_2$OY, —C≡CY and —CY═CHY, where the double bond may have the cis or trans stereochemical configuration, and where Y is selected from the group consisting of hydrogen, methyl, —CR$^5$O and a radical of the structure,

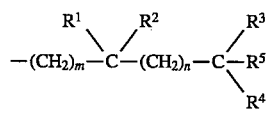

where m and n, independently, represent the integers from 0 to 5, where $R^1$ is selected from the group consisting of hydrogen, hydroxy, protected-hydroxy, fluoro, trifluoromethyl, and $C_{1-5}$-alkyl, which may be straight chain or branched and, optionally, bear a hydroxy or protected-hydroxy substituent, and where each of $R^2$, $R^3$ and $R^4$, independently, is selected from the group consisting of hydrogen, fluoro, trifluoromethyl and $C_{1-5}$ alkyl, which may be straight-chain or branched, and optionally bear a hydroxy or protected-hydroxy substituent, and where $R^1$ and $R^2$, taken together, represent an oxo group, or an alkylidene group $=CR_2R_3$, or the group $-(CH_2)_p-$, where p is an integer from 2 to 5, and where $R^3$ and $R^4$, taken together, represent an oxo group, or the group $-(CH_2)_q-$, where q is an integer from 2 to 5, and where $R^5$ represents hydrogen, hydroxy, protected-hydroxy, or $C_{1-5}$ alkyl.

2. The method of claim 1 where the compound is administered orally.

3. The method of claim 1 where the compound is administered parenterally.

4. The method of claim 1 where the compound is administered transdermally.

5. The method of claim 1 where the compound is administered in a dosage of from 0.5 µg to 50 µg per day.

* * * * *